(12) United States Patent
Brunengo et al.

(10) Patent No.: US 7,414,130 B2
(45) Date of Patent: Aug. 19, 2008

(54) INTEGRATED PROCESS FOR UREA AND MELAMINE PRODUCTION

(75) Inventors: Paolo Brunengo, Lugano (CH); Federico Zardi, Breganzona (CH)

(73) Assignee: Urea Casale S.A. (CH)

( * ) Notice: Subject to any disclaimer, the term of this patent is extended or adjusted under 35 U.S.C. 154(b) by 26 days.

(21) Appl. No.: 11/777,842

(22) Filed: Jul. 13, 2007

(65) Prior Publication Data

US 2007/0282102 A1  Dec. 6, 2007

Related U.S. Application Data

(63) Continuation of application No. 10/595,349, filed as application No. PCT/EP2004/008943 on Aug. 10, 2004, now abandoned.

(30) Foreign Application Priority Data

Feb. 20, 2004 (EP) ............... PCT/EP2004/001718

(51) Int. Cl.
*C07D 251/60* (2006.01)

(52) U.S. Cl. ..................................... 544/201

(58) Field of Classification Search .................. 544/201
See application file for complete search history.

(56) References Cited

U.S. PATENT DOCUMENTS

| 6,114,579 | A  | * | 9/2000 | Van Wijck |
| 6,586,629 | B1 | * | 7/2003 | Coufal |
| 7,094,927 | B2 | * | 8/2006 | Tjioe et al. |

FOREIGN PATENT DOCUMENTS

| DE | 1 468 207 A | * | 11/1968 |
| DE | 20 53 358 A | * | 5/1972 |
| GB | 1 148 767 A | * | 4/1969 |

* cited by examiner

*Primary Examiner*—Peter G O'Sullivan
(74) *Attorney, Agent, or Firm*—Akerman Senterfitt

(57) ABSTRACT

In an integrated process for urea and melamine production, urea is produced in a urea plant (12) comprising a high pressure urea synthesis section (15) and a urea recovery section (16) for separating urea from a carbamate aqueous solution, and melamine is produced in a melamine plant (11) wherein off-gases resulting as byproducts of the melamine synthesis are discharged therefrom at a pressure of at least 2 bar and recycled to the high pressure urea synthesis section (15).

8 Claims, 2 Drawing Sheets

INTEGRATED PROCESS FOR UREA AND MELAMINE PRODUCTION

This application is a continuation of U.S. Ser. No 10/595,349, filed 11 Apr. 2006, now abandoned, which is a 371 of PCT/EP04/08943,filed 10 Aug. 2004.

TECHNICAL FIELD

The present invention relates to a process for the integrated production of urea and melamine.

In particular, the present invention concerns a process of the above-identified type, wherein urea is produced in a urea plant comprising a high pressure urea synthesis section and a urea recovery section and wherein the off-gases resulting as by-products of the melamine synthesis are recycled to said high pressure urea synthesis section.

In the following description and subsequent claims, with the expression "high pressure urea synthesis section" it is intended to mean a section operated at a pressure of at least about 120 bar, generally between 130-260 bar.

More in particular, the process according to the present invention is of the type wherein the off-gases to be recycled have a pressure of at least 2 bar, generally between 2 and 30 bar.

The present invention is also concerned with an integrated plant for carrying out such a process.

As is known, in the field of urea and melamine there is increasingly felt the need of providing integrated processes wherein the off-gases produced in the melamine synthesis can be efficiently exploited for urea production.

PRIOR ART

In order to meet the above requirement, integrated processes have been proposed, wherein melamine is produced in a plant, so called melamine plant, using—as raw materials (reactants)-$NH_3$ and urea, the latter being produced in a plant for urea production, so called urea plant, to which the off-gases coming from the melamine plant and substantially containing $NH_3$ and $CO_2$, are recycled as raw materials (reactants).

According to these processes, the off-gases, generally discharged from the melamine plant at a pressure comprised between 2 and 30 bar, are appropriately treated before being fed into the urea plant.

In particular, the off-gases are condensed, at a pressure equal or lower than their discharge pressure, with a weak ammonia aqueous solution (ammonia concentration comprised between 0 to 15% by weight). The so obtained off-gas liquid solution is then fed to a waste water treatment section of the urea plant, generally operated at a pressure of about 2-5 bar, where $NH_3$ and $CO_2$ are recovered from the aqueous solution and recycled to the high pressure urea synthesis section, through the low pressure urea recovery section of the urea plant.

In the alternative, it has also been proposed to suitably compress the above off-gas liquid solution and recycle it directly to the high pressure synthesis section of the urea plant.

Although the above need is in some extent met by these processes, the latter are affected by several drawbacks.

In the first case, high energy consumption are required to separate $NH_3$ and $CO_2$ from the off-gas liquid solution in the waste water treatment section. Moreover, since the pressure in such a section is often much lower than the pressure of the off-gases discharged from the melamine plant, the off-gases have to be expanded before their condensation and recycle to the waste water treatment section of the urea plant, and thus there is also an energy waste in term of pressure loss.

In the second case, an additional, not negligible, amount of water is fed in the high pressure urea synthesis section through the recycled off-gas liquid solution. Since water is a by-product of the urea synthesis, its presence in the reactant feed is detrimental for the $CO_2$ conversion into urea. The urea conversion yield is thus negatively affected by the water contained in the recycled off-gas liquid solution with an ensuing increase in the energy consumption required to recover urea from the urea solution leaving the synthesis section and for recycling the unconverted reagents back to the synthesis section.

SUMMARY OF INVENTION

The technical problem underlying the present invention is to provide an integrated process for urea and melamine production having functional features such as to fully overcome the drawbacks set forth with respect to the prior art, wherein urea is produced at higher conversion yield and with lower energy consumption.

The above problem is solved, according to the invention, by an integrated process for urea and melamine production, wherein urea is produced in a urea plant comprising a high pressure urea synthesis section and a urea recovery section for separating urea from a carbamate aqueous solution, and melamine is produced in a melamine plant wherein off-gases resulting as by-products of the melamine synthesis are discharged therefrom at a pressure of at least 2 bar and recycled to said high pressure urea synthesis section, the process being characterized in that it further comprises the steps of:

feeding said off-gases coming from said melamine plant to an off-gas condensation section preferably operating at substantially the same pressure of the off-gases;

feeding said carbamate aqueous solution coming from said urea recovery section to said off-gas condensation section;

condensing said off-gases with said carbamate aqueous solution in said off-gas condensation section obtaining a concentrated carbamate aqueous solution;

feeding the so obtained concentrated carbamate aqueous solution to said high pressure urea synthesis section.

In case the pressure of the carbamate aqueous solution leaving the urea recovery section is lower than the operating pressure of the off-gas condensation section, then the process according to the present invention advantageously further comprises the step of:—compressing said carbamate aqueous solution coming from said urea recovery section to a pressure substantially corresponding to the operating pressure of said off-gas condensation section, previous to feeding it in such a section.

Moreover, in case the pressure of the off-gases discharged from the melamine plant is lower than the pressure of the urea synthesis section, then the process according to the present invention advantageously further comprises the step of:— compressing said concentrated carbamate aqueous solution coming from said off-gas condensation section to a pressure substantially corresponding to the operating pressure of said high pressure urea synthesis section, previous to feeding it in such a section.

The main advantage resulting by the process according to the present invention is that condensation of the off-gases is performed by exploiting the low amount of water already contained in the carbamate aqueous solution obtained in the urea recovery section of the urea plant and which is anyway recycled to the high pressure urea synthesis section. Therefore, contrary to the processes of the prior art—no additional amount of water is added to the off-gasses when recycling them from the melamine plant to the urea plant. It follows that, thanks to the invention, a more concentrated carbamate solution is recycled to the high pressure urea synthesis section of the urea plant with the consequence that the urea conversion yield is advantageously increased and the energy consumption required for recovering urea and recycling the unconverted reagents to the synthesis section are advantageously substantially decreased.

Further characteristics and advantages of the invention will result from the following description of an embodiment thereof given by way of non limiting example with reference to the attached drawings.

DETAILED DESCRIPTION OF A PREFERRED EMBODIMENT

Figure 1:
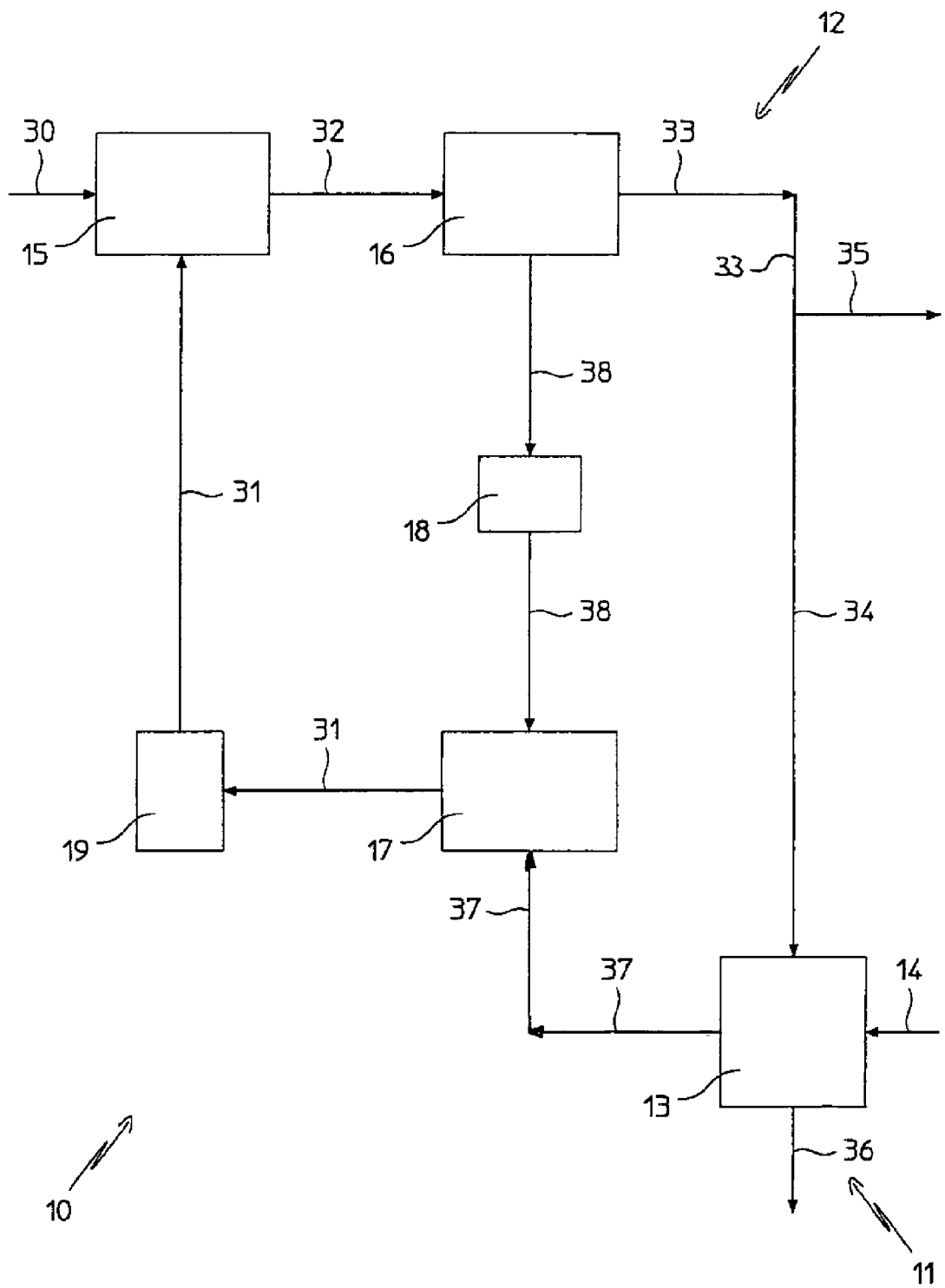
FIG. 1 schematically shows an integrated plant for urea and melamine production according to the process of the present invention.

With reference to FIG. 1, with number 10 is generally and schematically indicated an integrated plant for urea and melamine production according to the present invention. The integrated plant 10 comprises a plant 11 for the production of melamine and a plant 12 for the production of urea The melamine plant 11 of the present invention can be of the catalytic low pressure type (up to 70 bar) or of the non-catalytic high pressure type (above 70 bar), provided that the off-gases discharged from the melamine plant have a pressure of at least 2 bar. The plant 11 comprises a low pressure or high pressure melamine synthesis section 13.

Preferably, but non exclusively, the melamine plant 11 is of the non-catalytic high pressure type, wherein the off-gases discharged as by-products of the melamine synthesis have a pressure comprised between 3 and 30 bar, preferably between 20 and 25 bar. Of course, the off-gasses discharged from the melamine plant according to the present invention can also have a much higher pressure, depending on the pressure at which melamine is produced.

The urea plant 12 of the present invention is of the total recycle type, wherein urea is produced at a pressure of at least 120 bar, generally at about 130-260 bar, in a high pressure urea synthesis section 15 in fluid communication with a urea recovery section 16.

Generally, the urea recovery section 16 comprises (not shown) a medium pressure recovery section, operating at a pressure of about 15-30 bar and/or a low pressure recovery section, operating at a pressure of about 2-10 bar.

Preferably, the urea plant 12 is of the so called $CO_2$ or ammonia stripping type, with the high pressure urea synthesis section 15 operated at about 130-170 bar and comprising at least one urea synthesis reactor, stripper and carbamate condenser (not shown), connected one to the other so as to form a substantially isobaric loop.

For instance, the urea plant 12 of the present invention is of the $CO_2$ stripping type and the urea recovery section 16 only includes the low pressure section.

According to an advantageous feature of the present invention, the integrated plant 10 further comprises an off-gas condensation section 17 arranged between the plant 11 for melamine production and the plant 12 for urea production. In particular, as it will be described in detail hereinbelow, the off-gas condensation section 17 is in fluid communication with the melamine synthesis section 13, the urea recovery section 16 and the high pressure synthesis section 15.

Figure 2:
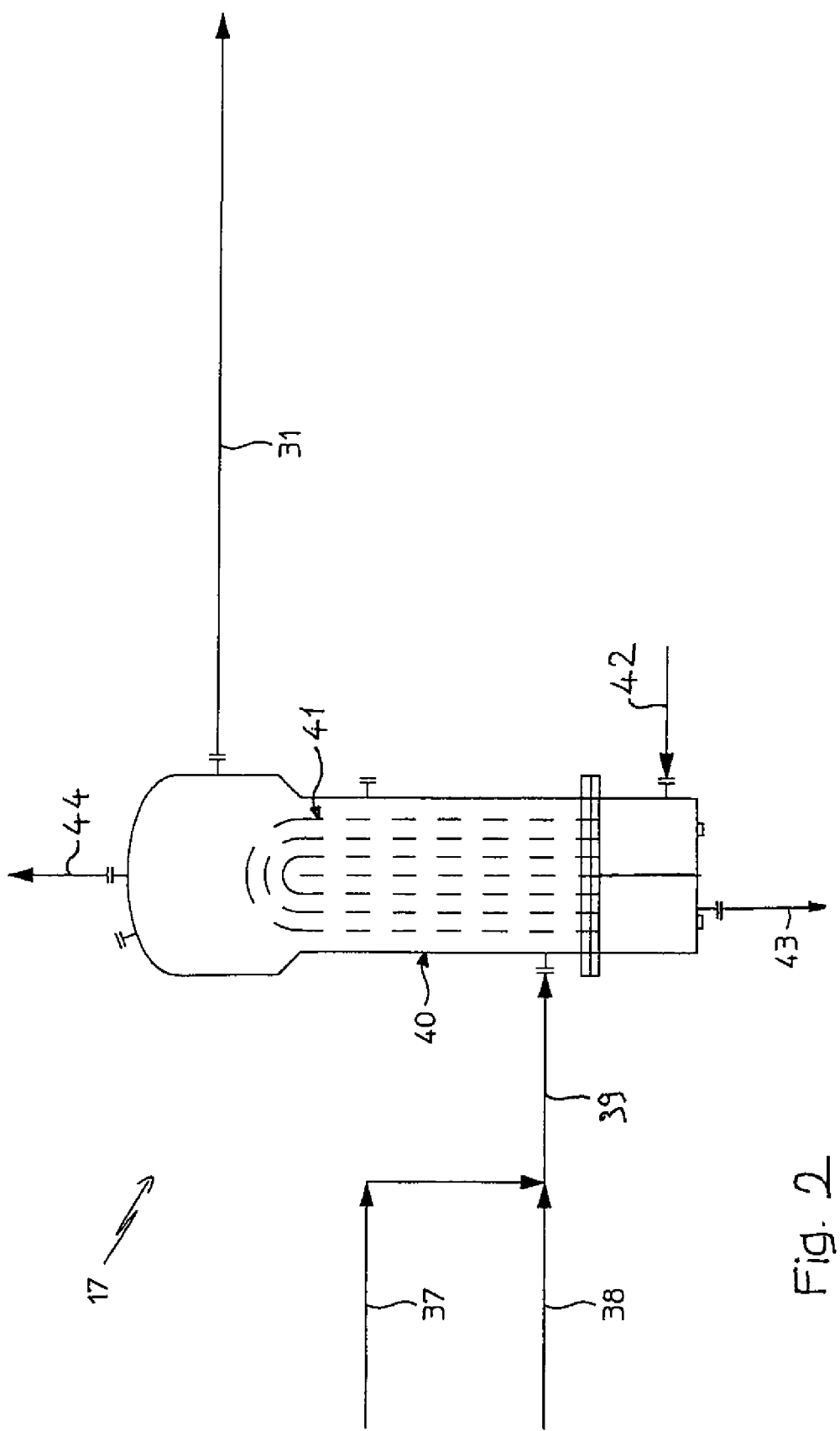
FIG. 2 schematically shows a detail of the integrated plant for urea and melamine production of FIG. 1.

As shown in FIG. 2, the off gas condensation section 17 comprises at lest one condenser apparatus 40, which in the present example comprises a tube bundle 41 heat exchanger.

Moreover, depending on the pressure of the solutions leaving the urea recovery section 16 and the off-gas condensation section 17, respectively, the integrated plant 10 of the invention optionally further comprises a first compression section 18, arranged between and in fluid communication with the urea recovery section 16 and the off-gas condensation section 17, and a second compression section 19, arranged between and in fluid communication with the off-gas condensation section 17 and the high pressure urea synthesis section 15. Compression sections 18 and 19 generally comprise at least one compressor or pump (not shown) for liquid flow of the conventional type.

The operation of the integrated plant 10 according to the invention is described hereinbelow.

CO2 and ammonia are fed to the high pressure urea synthesis section 15 of the urea plant 12 through flow line 30. Section 15 is also fed with a flow of concentrated carbamate aqueous solution, which will be described in greater details in the following description, through flow line 31.

In the high pressure urea synthesis section 15, the above reactants are made to react and a urea solution comprising urea, ammonium carbamate, free ammonia and water is obtained.

The urea solution leaves section 15 through flow line 32 and is fed to the urea recovery section 16, where it is further treated in order to separate urea from the other components of the solution (mainly water and unconverted reactants).

A concentrated urea solution, for instance comprising about 70% by weight of urea, is then discharged, through line 33, from the urea recovery section 16 and at least in part used as reactant in the plant 11 for melamine production.

In the alternative, urea is fed to the melamine synthesis section 13 of the melamine plant 11 in the form of melt urea coming from a urea finishing section (not shown) provided downstream to the urea recovery section 16.

To this aim, the concentrated urea solution, or a portion thereof, is fed, through line 34, to the melamine synthesis section 13. In the example of FIG. 1, not all the urea produced is used for the melamine synthesis and thus a portion of the concentrated urea solution is fed, through line 35, to a concentration section (not shown) of the urea plant 12 for further urea purification in order to produce for instance urea prills or granules.

To control the melamine synthesis, section 13 can optionally also be fed with an additional flow of ammonia, indicated in FIG. 1 by flow line 14.

From the melamine synthesis section 13, a melamine solution is discharged, through line 36, for further processing such as cooling (not shown), where melamine is converted into a powder and exits the plant 11.

Moreover, $CO_2$ and $NH_3$ off-gases are also obtained in section 13, as by-products of the melamine synthesis and leaves section 13 through flow line 37. Generally, before leaving the melamine synthesis section 13, the off-gases are suitably washed (scrubbed), not shown, with the feed concentrated urea solution in order to remove possible liquid melamine entrained in such gases.

Advantageously, the so obtained off-gases are then fed, through flow line 37, to the off-gas condensation section 17 of the integrated plant 10 of the present invention.

The off-gas condensation section 17 is father advantageously fed with a carbamate aqueous solution coming from the urea recovery section 16 of the urea plant 12, through a flow line 38.

This carbamate aqueous solution comprises at least part of the above-mentioned water and the unconverted reactants that have been separated from the urea solution in the urea recovery section 16. In the field, such a solution is commonly called recycle carbamate solution since it is the solution that is recycled (suitably compressed) to the high pressure urea synthesis section. An example of composition of the carbamate aqueous solution according to the present invention comprises: 20-40% by weight of ammonia, 20-40% by weight of $CO_2$ and the rest water. The amounts of these components can vary depending on the urea synthesis process.

Preferably, the off-gas condensation section 17 is operated at substantially the same pressure as the pressure of the off-gases leaving the melamine synthesis section 13.

In case the pressure of the off-gases coming from the melamine synthesis section 13 is higher than the pressure of the carbamate aqueous solution discharged from the urea recovery section 16, the latter is advantageously compressed in the first compression section 18 to the pressure of such off-gases i.e. to the operating pressure of the off-gas condensation section 17.

In the off-gas condensation section 17, the off-gases coming from the melamine synthesis section 13 and the carbamate aqueous solution coming from the urea recovery section are mixed together and fed through line 39 to the condenser apparatus 40. In the condenser apparatus 40, the off-gases are completely condensed (apart for a negligible amount of inert components non condensable) in the carbamate aqueous solution by indirect heat exchange with a cooling fluid (such as water), thus advantageously obtaining a concentrated carbamate aqueous solution.

According to the present example, the mixture of off-gases and carbamate aqueous solution fed to the condenser apparatus 40 is made to flow on the external side of the tube bundle 41 (mantel side), while the cooling fluid, which is fed to the condenser apparatus 40 through line 42 and is discharged therefrom through line 43, is made to flow within the tube bundle 41 (tube side).

In alternative embodiments of the present invention (not shown), the off-gases and the carbamate aqueous solution can be mixed together before being fed to the off-gas condensation section 17 or they can be fed directly and separately to the condenser apparatus 40, without being previously mixed.

The so obtained concentrated carbamate aqueous solution is then recycled to the high pressure synthesis section 15 through flow line 31, while the negligible amount of uncondensed inert components exits the condenser apparatus 40 through line 44. In particular, the concentrated carbarnate aqueous solution is recycled to one of the unit presents in the high pressure synthesis section 15, such as the synthesis reactor, the stripper or the carbamate condenser.

Should, as it is often the case, the operating pressure of the high pressure synthesis section 15 be higher than the operating pressure of the off-gas condensation section 17, then the concentrated carbamate aqueous solution leaving such a condensation section 17 is advantageously compressed in the second compression section 19 to the operating pressure of the urea synthesis section 15.

In integrated plant 10, the flow lines indicated in FIGS. 1 and 2 by reference signs 14, 30-39, 42-44 schematically represent connecting ducts or pipes of conventional type.

The plant 10 described above is particularly suitable for carrying out the integrated process for urea and melamine production according to the present invention, wherein urea is produced in the urea plant 12 comprising the high pressure urea synthesis section 15 and the urea recovery section 16 for separating urea from a carbamate aqueous solution, and melamine is produced in the melamine plant 11 wherein off-gases resulting as by-products of the melamine synthesis are discharged therefrom at a pressure of at least 2 bar and recycled to said high pressure urea synthesis section 15, the process being characterized in that it further comprises the steps of:

feeding said off-gases coming from said melamine plant 11 to the off-gas condensation section 17 preferably operating at substantially the same pressure of the off-gases;

feeding said carbamate aqueous solution coming from said urea recovery section 16 to said off-gas condensation section 17;

condensing said off-gases with said carbamate aqueous solution in said off-gas condensation section 17 obtaining a concentrated carbamate aqueous solution; and feeding the so obtained concentrated carbamate aqueous solution to said high pressure urea synthesis section 15.

According to another aspect of the invention, the present process can be suitable carried out also for the revamping or retrofitting of pre-existing urea and melamine plants as well as for the modification of pre-existing integrated plants for urea and melamine production.

In this case, and in addition to the advantages set forth above, it is worth noting that thanks to the present invention, and in particular to the feature of condensing the off-gases of the melamine plant with the carbamate aqueous solution discharged from the urea recovery section so as to obtain a concentrated carbamate aqueous solution, which is recycled to the high pressure urea synthesis section, it is not required to modify the equipment of the pre-existing high pressure urea synthesis section, such as the high pressure synthesis reactor, stripper and condenser.

The invention thus conceived is susceptible to further embodiments and modifications all falling within the skill of the man skilled in the art and, as such, falling within the scope of protection of the invention itself, as it is defined by the following claims

The invention claimed is:

1. An integrated process for urea and melamine production, wherein urea is produced in a urea plant of the so-called $CO_2$ or ammonia stripping type comprising a high pressure urea synthesis section operated at about 130-170 bar and comprising at least one urea synthesis reactor, stripper and carbamate condenser, connected one to the other so as to form a substantially isobaric loop, and a urea recovery section for separating urea from a carbamate aqueous solution, and wherein melamine is produced in a melamine plant wherein off-gases resulting as by-products of the melamine synthesis are discharged therefrom at a pressure between 2 and 30 bar and recycled to said high pressure urea synthesis section, the process comprising the steps of:

feeding said off-gases coming from said melamine plant to an off-gas condensation section operated at a pressure substantially equal to the pressure of said off-gases;

feeding said carbamate aqueous solution coming from said urea recovery section to said off-gas condensation section;

condensing said off-gases with said carbamate aqueous solution in said off-gas condensation section obtaining a concentrated carbamate aqueous solution; and feeding the so obtained concentrated carbamate aqueous solution to said high pressure urea synthesis section.

2. Process according to claim 1, wherein said carbamate aqueous solution coming from said urea recovery section is directly fed to said off-gas condensation section.

3. Process according to claim 1, wherein it further comprises the step of: compressing said carbamate aqueous solution coming from said urea recovery section to a pressure substantially corresponding to the operating pressure of said off-gas condensation section, previous to feeding it in such a section.

4. Process according to claim 1, wherein said concentrated carbamate aqueous solution is directly fed to said high pressure urea synthesis section.

5. Process according to claim 1, wherein it further comprises the step of: compressing said concentrated carbamate aqueous solution coming from said off-gas condensation section to a pressure substantially corresponding to the operating pressure of said high pressure urea synthesis section, previous to feeding it in such a section.

6. An integrated plant for urea and melamine production, comprising:
- a urea production plant of the so-called $CO_2$ or ammonia stripping type comprising a high pressure urea synthesis section comprising at least one urea synthesis reactor, stripper and carbamate condenser, connected one to the other so as to form a substantially isobaric loop, and a urea recovery section for separating urea from a carbamate aqueous solution;
- a melamine production plant comprising a melamine synthesis section wherein off-gases resulting as by-products of the melamine synthesis are discharged therefrom at a pressure of between 2 and 30 bar and recycled to said high pressure urea synthesis section;
- an off-gas condensation section arranged between said melamine production plant and said urea production plant and in fluid communication with said melamine synthesis section, said urea recovery section and said high pressure synthesis section;
- connecting means for feeding said off gases coming from said melamine synthesis section to said off-gas condensation section;
- connecting means for feeding said carbamate aqueous solution coming from said urea recovery section to said off-gas condensation section, wherein said off-gases are condensed with said carbamate aqueous solution obtaining a concentrated carbamate aqueous solution; and
- connecting means for feeding the so obtained concentrated carbamate aqueous solution to said high pressure urea synthesis section.

7. Plant according to claim 6, wherein it further comprises a first compressor section, arranged between and in fluid communication with said urea recovery section and said off-gas condensation section for compressing said carbamate aqueous solution coming from said urea recovery section to a pressure substantially corresponding to the operating pressure of said off-gas condensation section.

8. Plant according to claim 6, wherein it further comprises a second compression section, arranged between and in fluid communication with said off-gas condensation section and said high pressure urea synthesis section for compressing said concentrated carbamate aqueous solution coming from said off-gas condensation section to a pressure substantially corresponding to the operating pressure of said high pressure urea synthesis section.

* * * * *